US006956120B2

(12) United States Patent
Ikewaki et al.

(10) Patent No.: US 6,956,120 B2
(45) Date of Patent: Oct. 18, 2005

(54) β-1.3-1.6 GLUCAN (*AUREOBASIDIUM* MEDIUM)

(75) Inventors: Nobunao Ikewaki, Nobeoka (JP); Noboru Fujii, Miyazaki (JP); Takashi Onaka, Bizen (JP)

(73) Assignee: Yasushi Onaka, Bizen (JP)

( * ) Notice: Subject to any disclaimer, the term of this patent is extended or adjusted under 35 U.S.C. 154(b) by 0 days.

(21) Appl. No.: 09/986,535

(22) Filed: Nov. 9, 2001

(65) Prior Publication Data

US 2002/0082418 A1 Jun. 27, 2002

(30) Foreign Application Priority Data

Nov. 9, 2000 (JP) ........................................ 2000-342310

(51) Int. Cl.$^7$ ................................................ C07H 1/00
(52) U.S. Cl. ............... 536/123.12; 536/536; 536/123.1; 424/70.1; 424/70.13; 424/401; 424/439; 424/440; 424/442; 514/54; 426/648; 426/656; 426/658; 435/723; 435/74; 435/101; 435/102
(58) Field of Search ................................ 424/401, 439, 424/440, 441, 442, 70.1, 70.13; 514/54; 426/648, 656, 658; 435/72, 74, 101, 102; 536/1.1, 119, 115, 124, 123.1, 123.12

(56) References Cited

U.S. PATENT DOCUMENTS 5,789,579 A    8/1998  Fujii et al. .................. 536/119

FOREIGN PATENT DOCUMENTS

| JP | 62205008 A | * | 9/1987 | ............ A61K/7/00 |
| JP | 06146036 A | * | 5/1994 | ............ C23G/1/06 |
| JP | 06340701 A | * | 12/1994 | ............ C08B/37/00 |

OTHER PUBLICATIONS

Finkelman, Malcolm A. J. et al., "Synthesis of Beta–glucan by cell–free extracts of *Aureobasidium pullulans*," Canadian Journal of Microbiology, 1987, 33 (2), 123–127.*
Hamada, Nobutake et al., "The Structure of the Carbohydrate Moiety of an Acidic Polysaccharide Produced by *Aureobasidium* sp. K–1," Agric. Biol. Chem, 1983, 47 (6), 1167–1172.*
Abel et al., "Stimulation of Human Monocyte β–Glucan Receptors by Glucan Particles Induces Production of TNF–α and IL–1β," Int. J. Immunopharmacology, vol. 14, No. 8, 1992, pp. 1363–1373.
Czop et al., "Isolation and Characterization of β–Glucan Receptors on Human Mononuclear Phagocytes," J. Exp. Med., vol. 173, Jun. 1991, pp. 1511–1520.
Czop et al., "Phagocytosis of Particulate Activators of the Human Alternative Complement Pathway Through Monocyte β–Glucan Receptors," Biochemistry of the Acute Allergic Reations: Fifth International Symposium, Jun. 20–21, 1988, pp. 287–296.

Di Renzo et al., "The function of human Nk cells is enhanced by β–gulcan, a ligand of CR3 (CD11b/CD18)*," Eur. J. Immunol., 1992, 21, pp. 1755–1758.
Elstad et al., "CD11b/CD18 Integrin and a β–glucan Receptor Act in Concert to Induce the Synthesis of Platelet–Activating Factor by Monocytes1," J. Immunol. vol. 152, 1994, pp. 220–230.
Hetland et al., "Protectived Effect of β–Glucan Against Mycobacterium bovis, BCG Infection in BALB/c Mice," Scand. J. Immunol., 47, 1998, pp. 548–553.
Jespersgaard et al., "Protective Immunity against *Streptococcus mutans* Infection in Mice after Intranasal Immunization with the Glucan–Binging Region of S. mutans Glucosyltransferase," Infection and Immunity, vol. 67, No. 12, Dec. 1999, pp. 6543–6549.
Kay et al., "Enhancement of human monocyte β–glucan receptors by glucocorticoids," Immunology, 81, 1994, pp. 96–102. Ross et al., "Specificity of Membrane Complement Receptor Type Three ($CR_3$) for β–Glucans[1]," Complement 4, 1987, pp. 61–74.
Komatsu et al., "Host–Mediated Antitumor Action of Schizophylian, A Glucan Produced by Schizophyllum Commune," GANN, 60, Apr. 1969, pp. 137–144.
McLeish et al., "Bacterial phagocytosis activates extracellular signal–regulated kinase and p38 mitogen–activated protein kinase cascades in human neutrophils," Journal of Leukocyte Biology, vol. 64, Dec. 1998, pp. 835–844.
Moerk et al., "Effects of particulate and soluble (1–3)–β–glucans on Ca2+ Influx in NR8383 alveolar macrophages," Immunopharmacology 40, 1998, pp. 77–89.
Nobutake, Kobunshi Kako. (Polymer Applications), Kobunshi Kankokai., vol. 36, No. 5, 1987, pp. 9–16.
Ol et al., "Structural Studies on "Isosclerotan", a New Glucan Isolated from Sclerotinia Fungus, by Physical, Chemical and Enzymatic Methods," Agr. Biol. Chem., vol. 30, No. 3, 1966, pp. 266–273.
Patchen et al., "Glucan–Induced Hemopoietic and Immune Stimulation: Therapeutic Effects in Sublethally and Lethally Irradiated Mice," Meth and Find Expti Clin Pharmacolo, 1986, 8(3), pp. 151–155.

(Continued)

*Primary Examiner*—James O. Wilson
*Assistant Examiner*—Patrick Lewis
(74) *Attorney, Agent, or Firm*—Oblon, Spivak, McClelland, Maier & Neustadt, P.C.

(57) ABSTRACT

*Aureobasidium* β-1,3–1,6 glucans and compositions containing such glucans, as well as methods of their preparation. *Aureobasidium* medium that contains β-1,3–1,6 glucans, particularly medium produced by *Aureobasidium* strain FERM P-18099. The β-glucans of the present invention have a variety of industrial and commercial uses, including applications in pharmaceutical or medical products or treatments, for the removal or control of environmental or microbiological contaminants, in cosmetics, and in nutritional products and foods.

11 Claims, 8 Drawing Sheets

OTHER PUBLICATIONS

Poutsiaka et al., "Cross–Linking of the β–Glucan Receptor on Human Monocytes Results in Interleukin–1 Receptor Antagonist But Not Interleukin–1 Production," Blood, vol. 82, No. 12, Dec. 15, 1993, pp. 3695–3700.

Ross et al., "Therapeutic intervention with complement and β–glucan in cancer," Immunopharmacology 42, 1999, pp. 61–74.

Ross et al., "Specificity of Membrane Complement Receptor Type Three (CR3) for β–Glucans1," Complement 4, 1987, pp. 61–74.

Singh et al., "Scleroglucan, an antitumor polysaccharide from Scierotium glucanicum," Carbohydrate Research, 37, 1974, pp. 245–247.

Smiley, "Microbial Polysaccharides—A Review," Food Technology, Sep. 1966, pp. 112–116.

Szczesniak et al., "Objective Characterization of the Mouth-feel of Gum Solutions," Journal of Food Science, vol. 27, No. 4, Jul.–Aug. 1962, pp. 381–385.

Teramoto, "Markedly increased plasma (1–3) β–glucan is a diagnostic and therapeutic indicator of Pneumocystis carinii pneumonla in a non–AIDS patient," Journal of Medical Microbiology, vol. 49, 2000, pp. 393–394.

Thornton et al., "Analysis of the Sugar Specificity and Molecular Location of the β–Glucan–Binding Lectin Site of Complement Receptor Type 3 (CD11b/SC18)," J. Immunol., vol. 156, 1996, pp. 1235–1246.

Wakshull et al., "PGG–Glucan, a soluble β–(1,3)–glucan, enhances the oxidative burst response, microbicidal activity, and activates an $NF-_kB$–like factor in human PMN: Evidence for a glycosphingolipid β–(1,3)–glucan receptor," Immunopharmacology 41, 1999, pp. 89–107.

Xia et al., "Generation of Recombinant Fragments of CD11b Expressing the Functional β–Glucan–Binding Lectin Site of CR3 (CD11b/CD18)[1]," J. Immunol. vol. 162, 1999, pp. 7285–7293.

Xia et al., "The β–Glucan–Binding Lectin Site of Mouse CR3 (CD11b/CD18) and its Function in Generating a Primed State of the Receptor That Mediated Cytotoxic Activation in Response to iC3b–Opsonized Target Cells[1]," The American Association of Immunologists, 1999, pp. 2281–2290.

Yan et al., "β–Glucan, a "Specific" Biologic Response Modifier That Uses Antibodies to Target Tumors for Cytotoxic Recognition by Leukocyte Complement Receptor Type 3 (CD11 b/CD18)[1]," J. Immunol., vol. 163, 1999, pp. 3045–3052.

Yoshioka et al., "Immunotoxicity of soluble β–glucans induced by indomethacin treatment," FEMS Immunology and Medical Microbiology, 21, 1998, pp. 171–179.

* cited by examiner

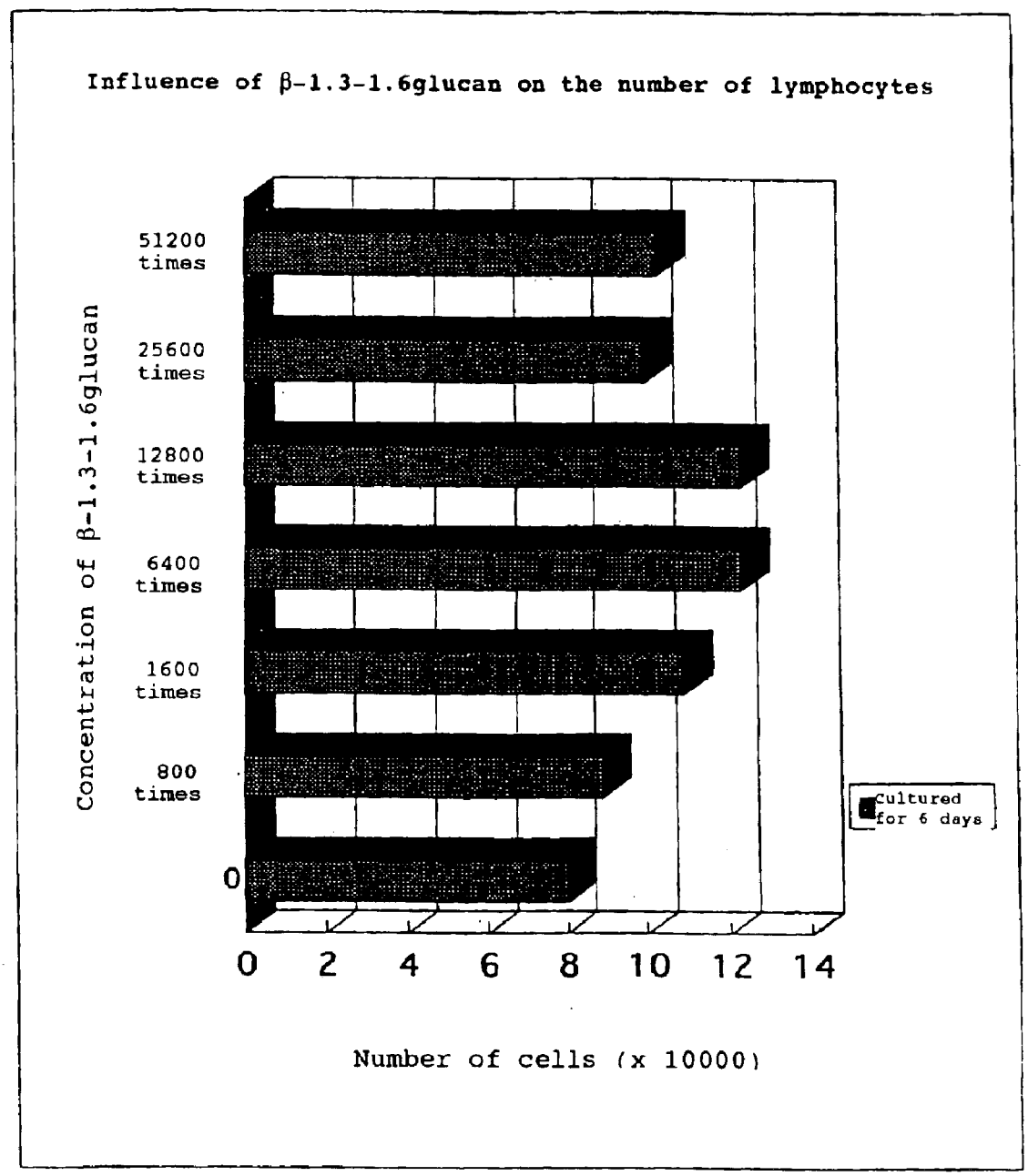
Fig.1 Influence of β-1.3-1.6glucan (Aureobasidium medium) on the number of lymphocytes in peripheral blood

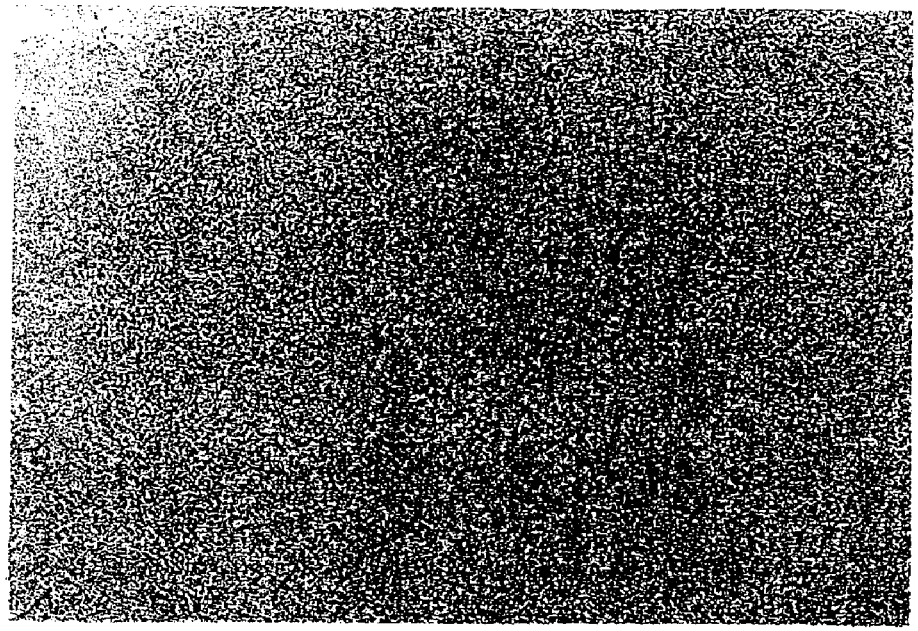
No addition
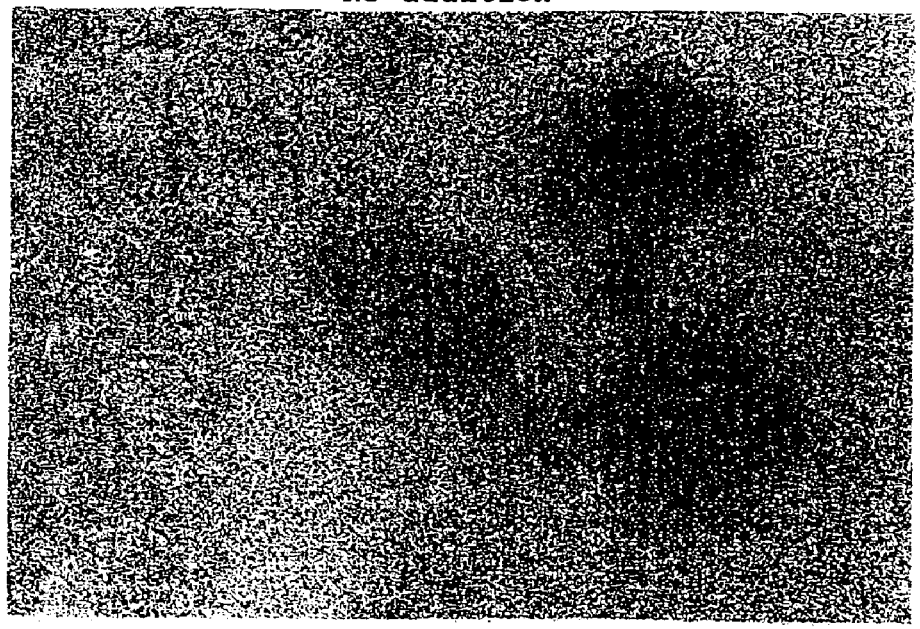
Addition with β-1.3-1.6glucan (Aureobasidium medium)
Fig.2: Photographs Morphological change of lymphocytes in peripheral blood with β-1.3-1.6glucan (Aureobasidium medium)

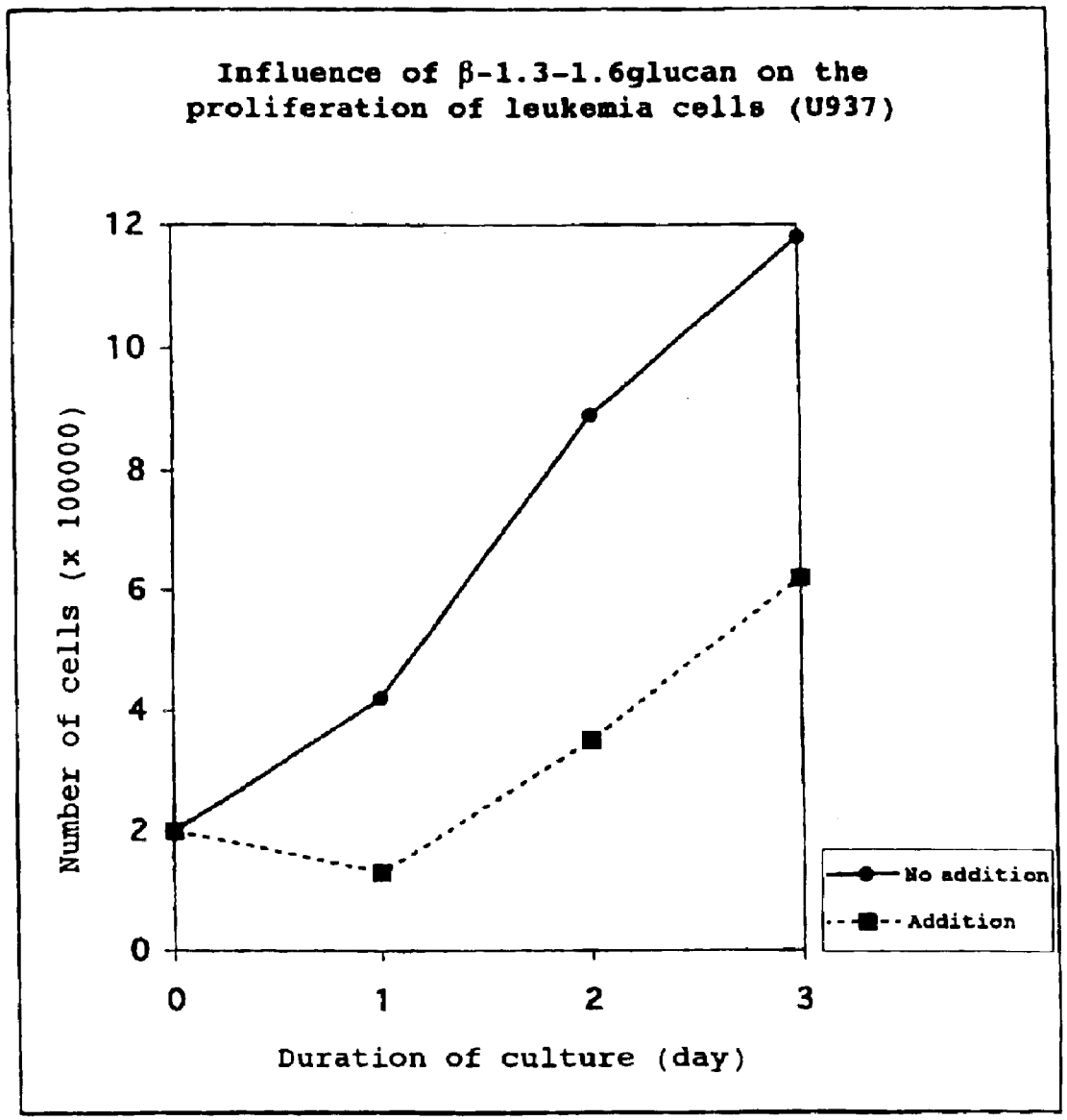
Fig.3 Influence of β-1.3-1.6glucan (Aureobasidium medium) on the proliferation of cancer cells

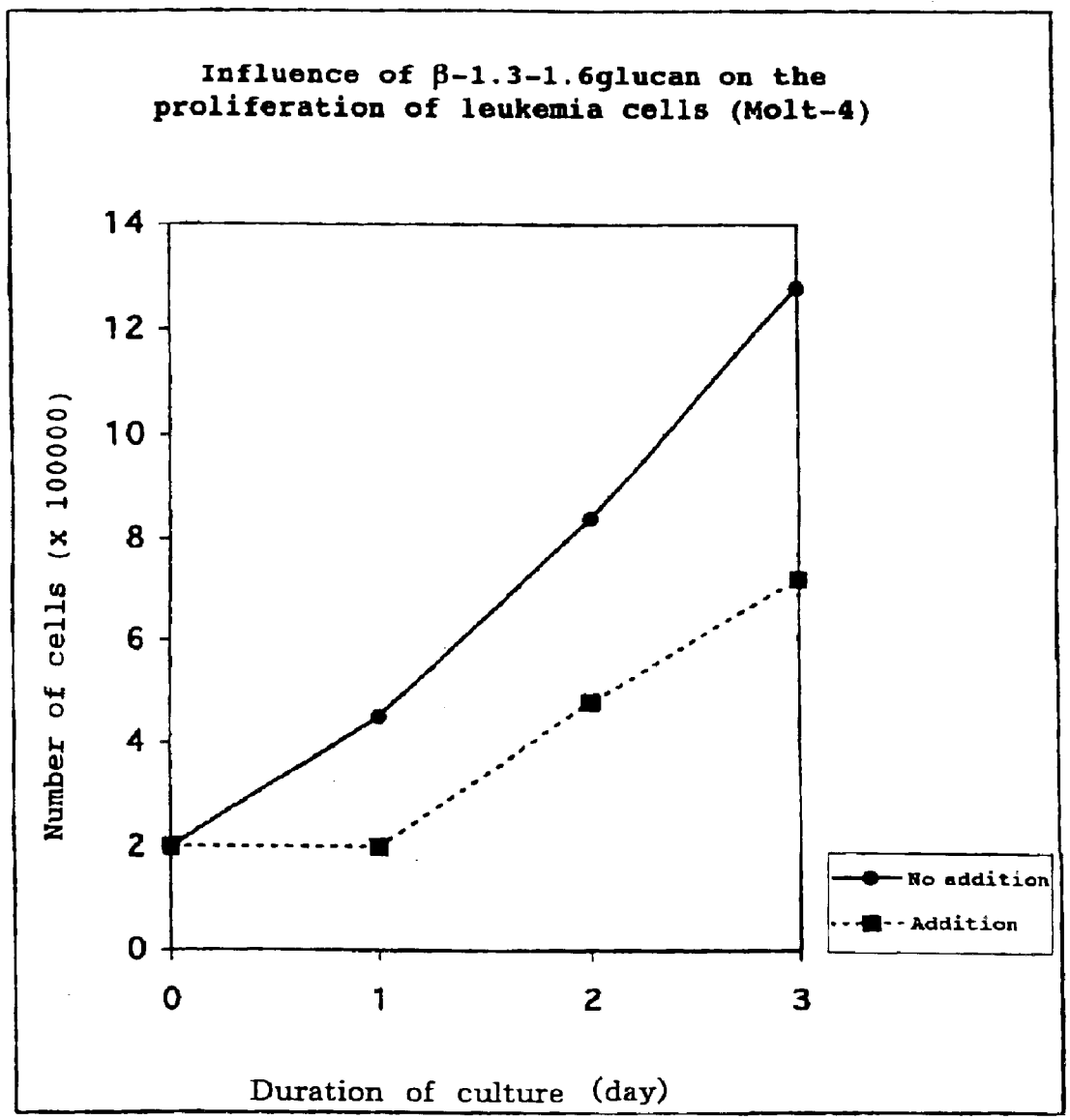
Fig.4 Influence of β-1.3-1.6glucan (Aureobasidium medium) on the proliferation of cancer cells

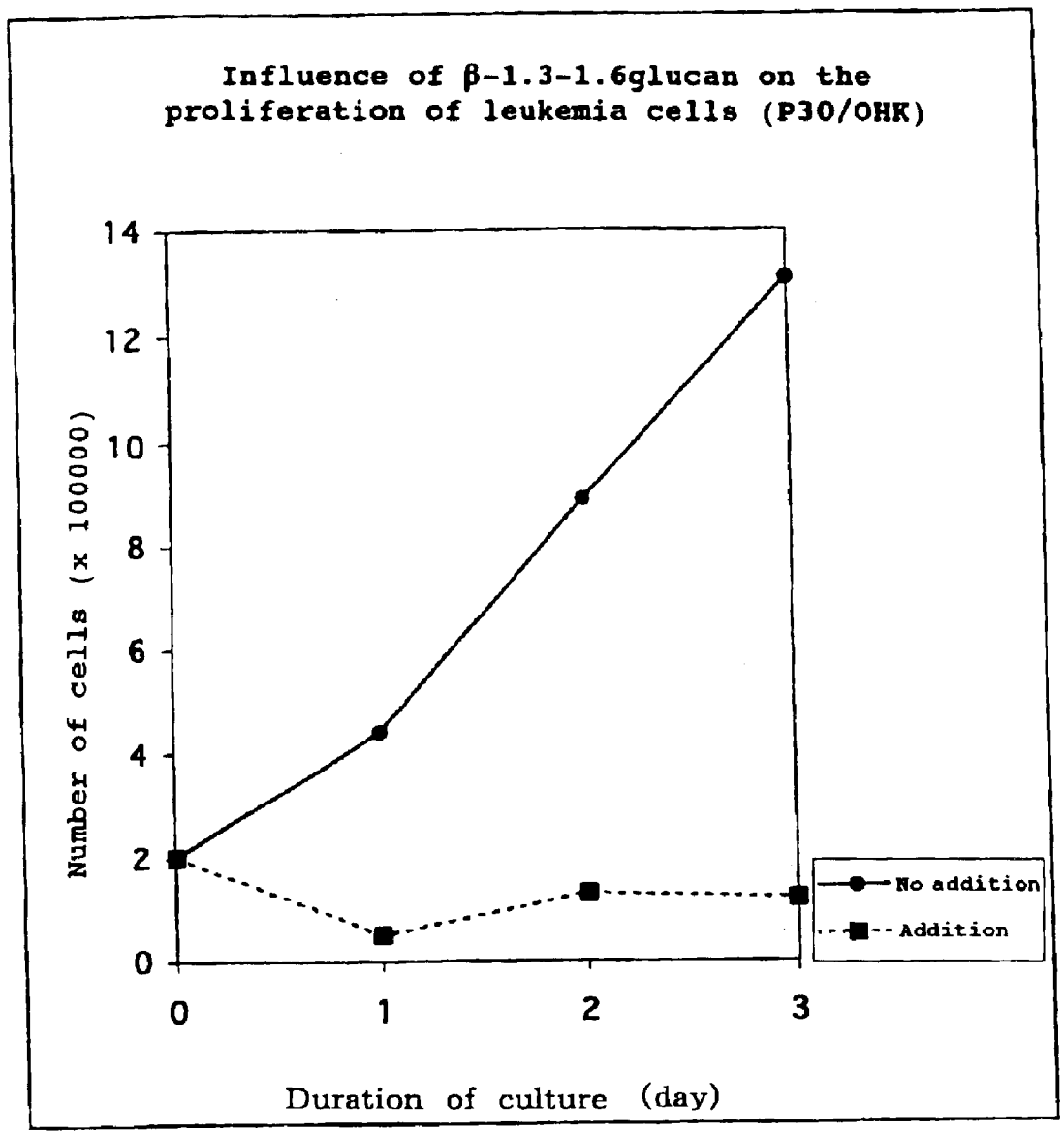
Fig.5 Influence of β-1.3-1.6glucan (Aureobasidium medium) on the proliferation of cancer cells

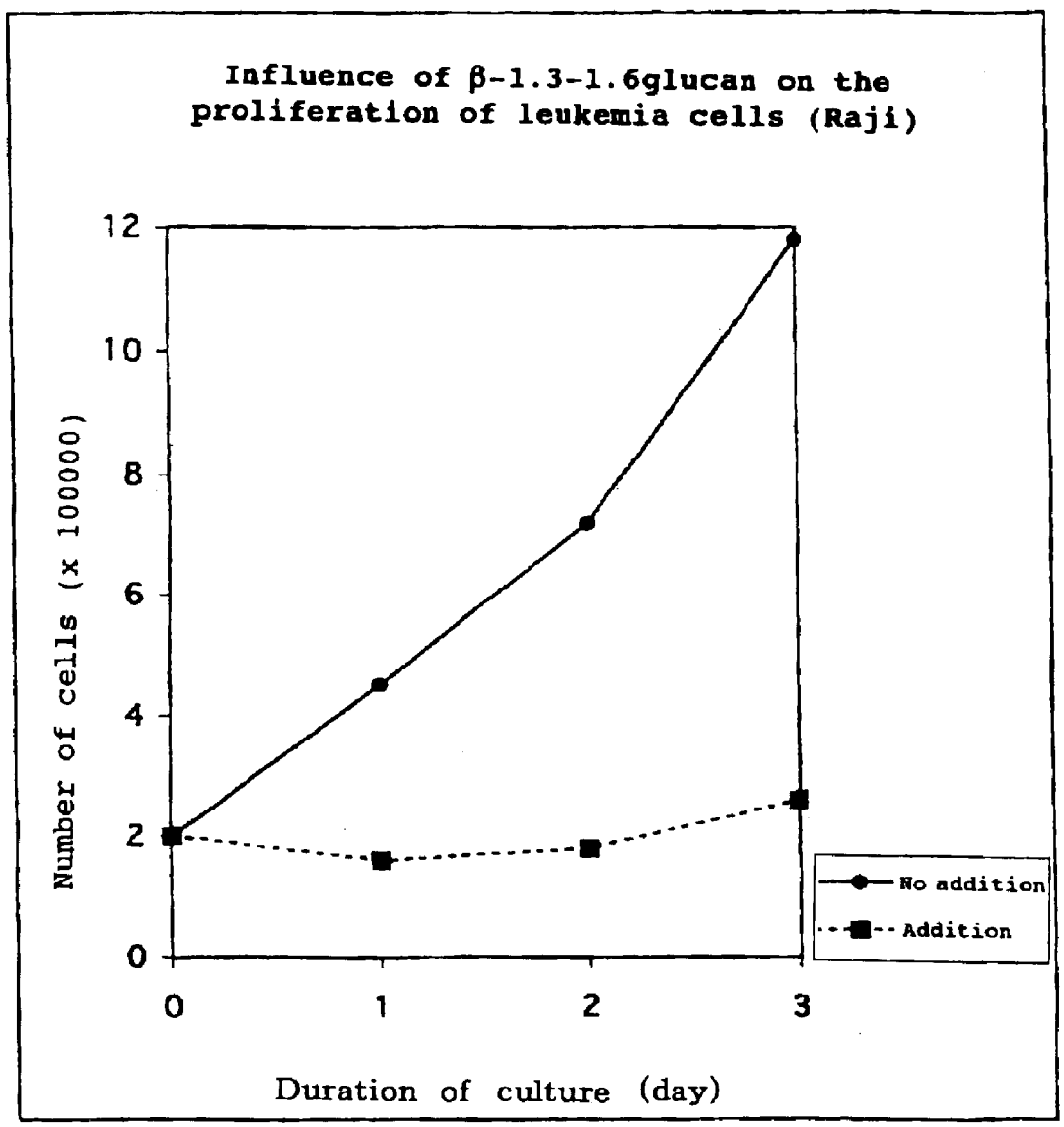
Fig.6 Influence of β-1.3-1.6glucan (Aureobasidium medium) on the proliferation of cancer cells

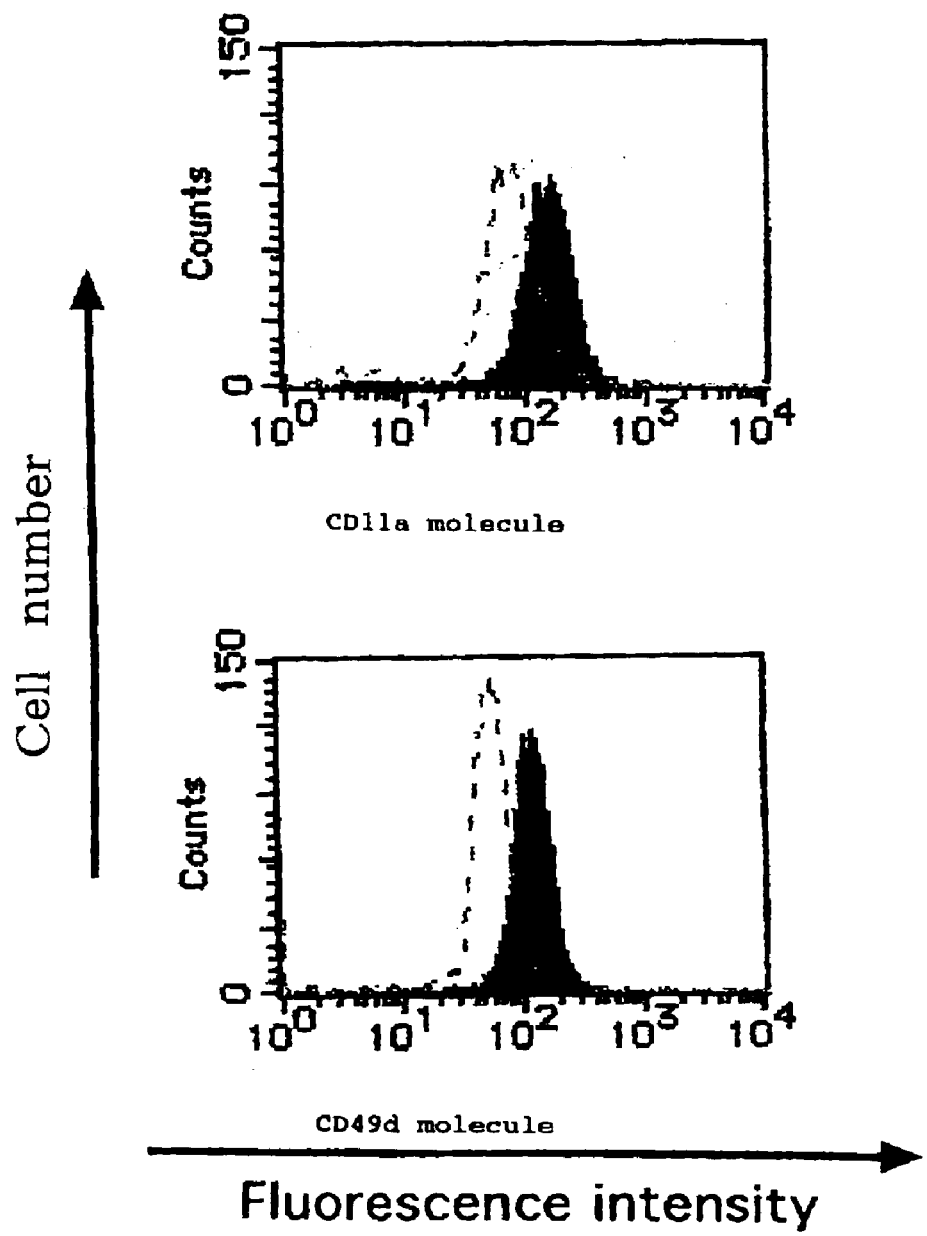
Fig.7 Influence of β-1.3-1.6glucan (Aureobasidium medium) on the dynamics of model cell surface molecules (receptor molecules) in monocyte/macrophage system
No addition: — / Addition with β-1.3-1.6glucan (Aureobasidium medium) ---

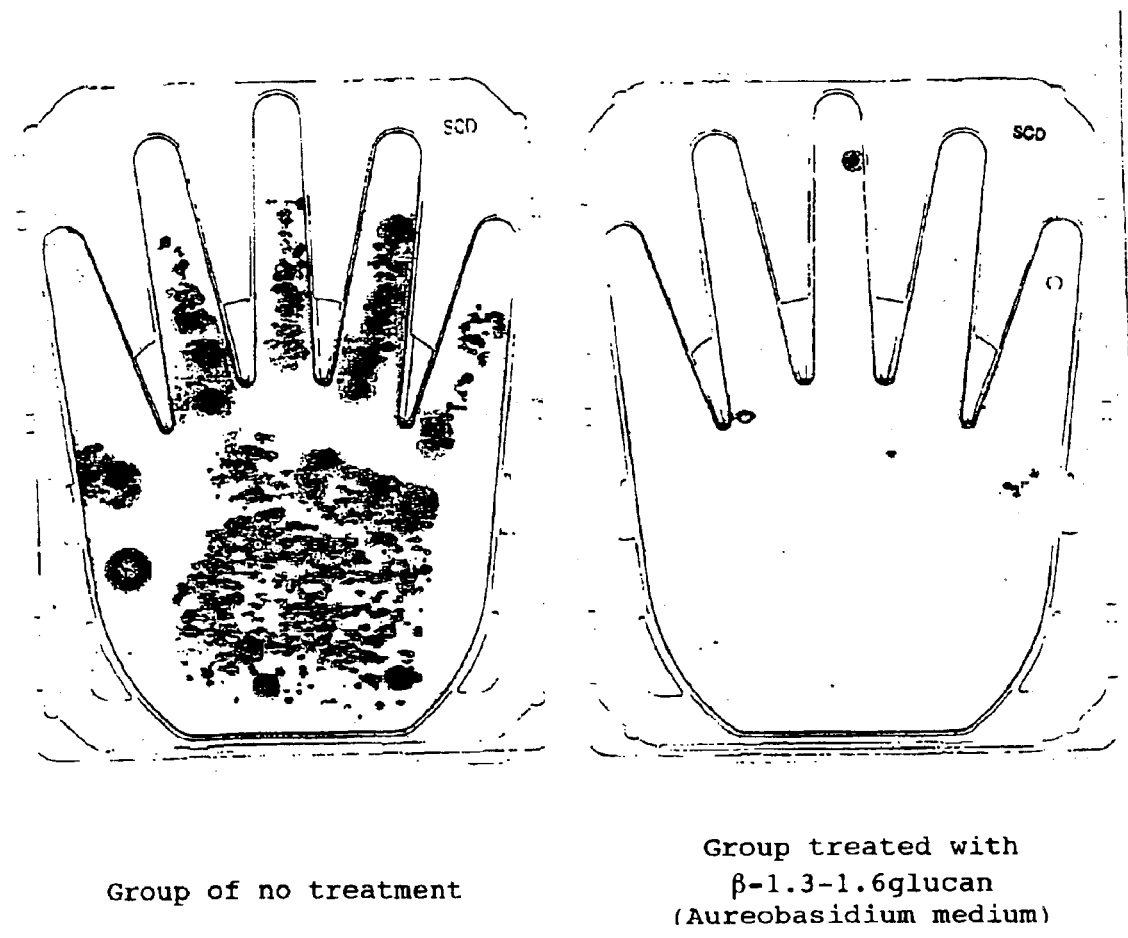
Group of no treatment
Group treated with
β-1.3-1.6glucan
(Aureobasidium medium)
Fig.8  Influence of β-1.3-1.6glucan (Aureobasidium medium) on the environmental microbes (proliferation)

β-1.3-1.6 GLUCAN (AUREOBASIDIUM MEDIUM)

BACKGROUND OF THE INVENTION

1. Field of the Invention

The invention relates to a particular type of β-glucan—a microbial polysaccharide composed of D-glucose in either straight or branched chains with glycosidic linkages. More specifically, the present invention is directed to industrial and commercial applications of a β-1,3–1,6-glucan appearing in the medium of the black yeast, *Aureobasidium*. *Aureobasidium* is one of several genera of black yeasts, characterized by mostly slow-growing, black, pasty colonies. β-1,3–1,6-glucans are complex acidic polysaccharides having a main chain comprising subunits having 1,3 linkages and branches at the 3- and 6-positions. The β-glucans of the present invention have a variety of industrial and commercial uses, including applications in pharmaceutical or medical products or treatments, for the removal or control of environmental or microbiological contaminants, in cosmetics, and in nutritional products and foods.

2. Description of the Related Art

Various microbial and fungal polysaccharides with different structures and diverse physiological properties are known. Such polysaccharides have been studied from a variety of different aspects, see e.g. Hamada Nobutake: Kobunshi Kako 36:9–16 (1987); and Ohno Naohito: J. Bacteria Japan 527 (2000).

Microbial polysaccharides are formed from different types of monosaccharide units, such as particular types of sugars, including glucose (dextrose, grape sugar) and fructose (fruit sugar). Glucans comprise units of glucose. However, depending on the type of linkage between these subunits, a glucan may be either an α-glucan or β-glucan, Oi et al., Agric. Biol. Chem. 30: 266 (1966).

Microbial polysaccharides may have unique physical properties and physiological activities. For instance, their physical properties can provide consistency, body and substance to foods. They can be utilized as thickening agents and as raw materials in semi-solid foods, such as jellies. Polysaccharides, such as curdlan, are utilized as antioxidant films, Szezesniak et al., J. Food Sci. 27: 381 (1962), Smiey, Food Technol 20: 112 (1966). Moreover, microbial polysaccharides which impart stability, water retention and dispensability may be used in a variety of products, including cosmetics, paints, fertilizers, papermaking, fibers, etc., Jeans, Extracellular Microbiol. Polysaccharides, Sanford et al. (eds), American Chemical Society, Washington, D.C. (1977).

On the other hand, other types of polysaccharides, such as dextran, are used for certain pharmaceutical or medical applications. For instance, dextran is utilized as a plasma substitute or blood flow improver. Polysaccharides, such as chizophyllan, scleroglucan, and curdlan have physiological activities that may be useful in treating diseases such as cancer, Komatsu et al., Gann 60: 137 (1969); Singh et al., Carbohydr. Res. 37: 245 (1974). In general, such polysaccharides do not act directly on cancer cells, but by enhancing immunity. Protein-containing polysaccharides of *Trametes versicolor* PSK, the polysaccharide lentinan of *Lentinus edodes* and the polysaccharide schizophyllan of *Schizophyllum commune* are used as immunotherapeutic drugs for cancer.

An acidic polysaccharide produced by strain FERM P-14228 is described by U.S. Pat. No. 5,789,579. This patent is directed to α-glucans having α-1.4 bonding, unlike the β-glucans of the present invention that have β-1,3–1,6 linkages.

β-glucans are found in mushrooms, such as *Agaricus* and *Lentinus*, various starches, cellulose, seaweeds, red algae, yeasts and other similar micro-organisms. Some types of β-glucans play a significant role in health maintenance, see Fujii Noboru: A miracle of β-glucan, Society for Study of Beta Glucan. The present inventors have found that β-1, 3–1,6 glucan (*Aureobasidium* medium) contains much higher quantities of β-glucan than mushrooms—over ten-times more.

Physiological Effects of β-glucans. Many studies have been made with respect to the physiological effects of β-glucans. In particular, the regulatory actions of these compounds on the vital balance and vital immune reaction have been studied. For instance, the protective effects of these compounds in cancer and infectious disease have been studied. Some types of β-glucans, which are of a different type from those of the present invention, have antitumor activities. For instance, these have been observed on 3LL solid tumor cells derived with methylcholanthrene-I in experimental animals, see Fujii Noboru, Shinohara Satoru: Report of the Department of Agriculture, Miyazaki University 33: 243 (1986).

Glucan Receptor. β-glucan receptors are known to be expressed on immunocompetent cells, such as monocytes and macrophages, see Czop et al., J. Exp Med 173: 1511 (1991), Xia et al., J. Immunol. 162: 7285 (1999), Czop, et al., Prog. Clin. Biol. Res. 297: 287 (1989). Certain β-glucans are known to induce the production of inflammatory cytokines from immunocompetent cells, for example, the interleukin 1 receptor antagonist (IL-1Ra) which is an antagonist of interleukin 1β (IL-1β), see Poutsiaka et al., Blood 82: 3695 (1993). It also induces the production of tumor necrosis factorα (TNF-α), interleukin 1β (IL-1β) and platelet activating factor (PAF), and the like, see Abel et al., Int. J. Immunopharmacol. 14: 1363 (1992), Elstad, et al., J. Immunol. 52: 220 (1994).

The molecular structure of the β-glucan receptor has been found to correspond to complement receptor 3 ("CR3") that binds complement component C3. Recently, this receptor has been shown to be an integrin type CD11b/CD18 molecule itself, see Ross, et al., Complement 4: 61 (1987), Thornton, et al., J. Immunol. 156: 1235 (1996). It has also been found that this CR3 (CD11 b/CD18) molecule is a receptor mainly manifested on the cell surface of monocytes and macrophages and in NK cells. NK cells activated by β-glucan bonding to the CD11b/CD18 molecule via this receptor (CR3) molecule are involved in the destruction and removal of cancer cells, see Di Renzo et al., Eur. J. Immunol. 21: 1755 (1991), Ross, et al., Immunopharmacology 42: 61 (1999), Yan, et al., J. Immunol. 163: 3045 (1999).

Signal transmission. The analysis of signal transmission modes from the β-glucan receptor has been studied. $Nf_kB$ plays a role as an intranuclear transmission substance of immuno-B-cyte which takes part closely in this signal transmission system, Wakshull et al., Immunopharmacology 41: 89 (1999). Moreover, in model experiments for the therapy of cancer, from the fact that β-glucan is a receptor (CD11b/CD18 molecule) of C3 component of complement, see Yan, et al., J Immunol 163: 3045 (1999), it is reported that the route via this receptor is effective for the destruction of cancer cells opsonized with specific antibody of cancer, see Xia et al., J. Immunol. 162: 2281 (1999).

Drug effects on glucan receptor. On the other hand, functional experiments between drugs having an influence on the immune reaction and β-glucan receptor are also being conducted, and new roles of β-glucan in the vital immune system have become clear in such ways that, in particular, β-glucan receptor (CD11b/CD18 molecule) accelerates its receptor function with glucocorticoid, and the like, see Yashioka et al., FEMS Immunol. Med. Microbiol. 21: 171 (1998), Kay, et al., Immunology 81: 96 (1994).

Glucan effects in vivo. The effects of β-glucans in vivo have also been investigated. Administration of a glucan increases the survival and longevity (macrobiotic effect) of mice exposed to lethal levels of radiation. This effect is attributed to hemopoietic effects of β-glucan and direction of immunocompetent cells into a maturation process, see Patchen et al., Methods Find. Exp. Clin. Pharmacol. 8: 151 (1986). In addition, β-glucans stimulate macrophage function and may thus provide protective effects against certain infectious diseases, such as tuberculosis, see Hetland et al., Scand. J. Immunol 47: 548 (1998). Immunization with the glucan-binding domain of Streptococcus mutans glucosyltransferase provides immunity against infection with Streptococcus mutans, see Jespersgaard et al., Infect. Immun. 67: 6543 (1999).

Immune enhancement with glucans and other substances. While some β-glucans may enhance certain components of the immune system, such as macrophage function, immunological enhancement is a complex phenomenon and at the cell level many intracellular transmission substances are involved in producing these effects. For instance, recently it has been found that mitogen activating protein kinase (MAPK) and calcium controlling the activation and management of immune system are closely involved in these phenomena, see McLeish, et al., J. Leukoc. Biol. 64: 835 (1998), Mork, et al., Immunopharmacology 40: 77 (1998).

β-glucan analogs and diagnosis. Clinically, β-glucan analogues in plasma in patients with pneumonia have been observed. For instance, β-glucan analogues increase in plasma in cases of Pneumocystis carinii pneumonia having no overt AIDS-like symptoms, see Teramoto et al., J. Med. Microbiol. 49: 393 (2000).

While some β-glucans were known to stimulate particular components of the cellular immune system, such as macrophage functions, the present inventors have found that the β-1,3–1,6 glucan (Aureobasidium medium) of the present invention exerts other specific functional activities, such as inducing increases in the numbers of lymphocytes, inducing DNA synthesis and cell division in lymphocytes, exerting direct effects on cancer cells, and directly inhibiting the proliferation of microbes.

SUMMARY OF THE INVENTION

The invention relates to an Aureobasidium medium containing β-1,3–1,6 glucan as a major component and a method of producing the same by culturing fungi that produce β-1,3–1,6 glucan of Aureobasidium. The unique functional properties of the β-glucans of the present invention, which include particular modulatory and regulatory effects on the immune system, make these products particularly advantageous for a variety of industrial and commercial applications. The glucans of the present invention may be used as present in Aureobasidium culture medium, which is preferably sterilized or filtered, or may be used after further purification. Such applications include use in pharmaceutical or medical products or treatments, in diagnostic products and methods, for the removal or control of environmental or microbiological contaminants, in chemical products, in cosmetics, and in nutritional products and foods.

The present inventors have discovered that β-1.3–1.6glucan (Aureobasidium medium) prepared according to the invention has unique physical properties and physiological activity quite different from those of other types of β-glucans. In particular, the β-1,3–1,6 glucan (Aureobasidium medium) of the present invention modulates and regulates the immune system. It has been found to have a specific effect on the production of interleukin-6 (IL-6) which is involved in controlling the number of lymphocytes in human peripheral blood, in cell division and in other aspects of immunity.

Moreover, the β-1,3–1,6 glucan (Aureobasidium medium) of the present invention effectively inhibited the proliferation of cancer cells, such as leukemia cells. While not being limited to a particular mechanism of action, it is considered that this effect may involve the programmed death of cancer (leukemia) cells or apoptosis. Thus, the β-1,3–1,6 glucan (Aureobasidium medium) of the present invention has advantageous applications for clinical therapy of cancer.

It has also been found that β-1,3–1,6 glucan (Aureobasidium medium) influences the expression or function of adhesion molecules involved in immunity. For instance, the inhibition of expression or down-regulation of integrin-type adhesion molecules, such as CD11a and CD49d, expressed in monocytic cells was recognized. This finding provides for application of β-1,3–1,6 glucan (Aureobasidium medium) in the treatment of various microbial diseases. For instance, the CD11a molecule is a receptor for rotavirus, which causes infant and child diarrhea. Since β-1,3–1,6 glucan (Aureobasidium medium) down-regulates the expression or function of CD11a molecules as shown in the example below, it may be used to prevent the attachment or adsorption of rotavirus, and prevent or ameliorate infections involving CD11a.

Moreover, the CD49d molecule is also an integrin type adhesion molecule and an immune function regulator. This molecule is considered to be strongly involved in the infiltration of T lymphocytes into the articular synovial membrane of patients having chronic articular rheumatism. Since the expression of CD49d molecule is also subject to the down-regulation with β-1,3–1,6 glucan (Aureobasidium medium), it may be used in methods for therapy of diseases such as chronic articular rheumatism and other autoimmune diseases, involving expression of CD49d. Thus, the β-1, 3–1,6 glucan (Aureobasidium medium) may exert anti-inflammatory effects.

Applicants have also discovered that apart from the advantageous immunological effects of β-1,3–1,6 glucan (Aureobasidium medium), that this substance may be used for preventing the propagation of environmental microbes. Thus, β-1,3–1,6 glucan (Aureobasidium medium) may be used as a novel antiseptic, preservative or antimicrobial agent. Such agents have application for maintaining personal cleanliness, for instance of the body, hands or feet, and as a portable disinfectant. Such a disinfectant may be used for persons who cannot bathe, such as the aged or infirm and for prevention of nosocomial infections. It may also be used to remove environmental pollutants.

As described and shown below, the present invention involving β-1,3–1,6 glucan (Aureobasidium medium) may be advantageously and safely used in medical and pharmaceutic products and methods, in foods and cosmetics and as an antiseptic or antimicrobial agent.

BRIEF DESCRIPTION OF THE DRAWINGS

FIG. 1 shows the influence of β-1,3–1,6 glucan (Aureobasidium medium) on the numbers of lymphocytes in peripheral blood.

FIG. 2, panels (a) and (b) compare the morphological changes in lymphocytes grown in control medium with those grown in medium containing β-1,3–1,6 glucan (Aureobasidium medium).

FIG. 3 shows the influence of β-1,3–1,6 glucan (Aureobasidium medium) on the proliferation of U937 leukemia cells.

FIG. 4 shows the influence of β-1,3–1,6 glucan (Aureobasidium medium) on the proliferation of Molt-4 leukemia cells.

FIG. 5 shows the influence of β-1,3–1,6 glucan on the proliferation of P30/OHK leukemia cells.

FIG. 6 shows the influence of β-1,3–1,6 glucan (Aureobasidium medium) on the proliferation of Raji leukemia cells.

FIG. 7, panels (a) and (b) show the influence of β-1,3–1,6 glucan (Aureobasidium medium) on cell surface molecules CD11a and CD49d, respectively.

FIG. 8, panels (a) and (b) show palm stamps of untreated hands and hands wiped with β-1,3–1,6 glucan (Aureobasidium medium), respectively. Black marks depict the growth of microorganisms.

DETAILED DESCRIPTION OF THE INVENTION

Aureobasidium medium that contains β-1,3–1,6 glucan may be produced by strains of Aureobasidium. Advantageously, strain FERM P-18099 may be used. This strain has been deposited at the:

Agency of Industrial Science and Technology Life Engineering Research Institute, Higashi 1-chome, 1–3, Tsukuba-shi, Ibaraki, 305–0046, Japan The characteristics of this strain are described below.

Properties, taxonomy and mycological features of FERM P-18099. FERM P-18099 is a black fungus used for preparing Aureobasidium medium that contains β-1,3–1,6 glucan as a major component. Its properties are as follows:

Scientific properties. This fungus produces high-molecular polysaccharide with high viscosity. This substance agglutinates easily with ethanol, making it possible to collect simply. Other purification methods, such as those described by U.S. Pat. No. 5,789,579 for purification of an α-type acid polysaccharide, may also be used. This polysaccharide is of β type, and is acidic polysaccharide having a main chain of 1,3 bond and branches from 3- and 6-positions. It contains carboxylic acids such as malic acid as organic acids and phosphoric acid. Moreover, it agglutinates easily with aluminum ions etc. This substance is also effective for the promotion of growth as a feed and the effluent treatment. It is effective as a food additive and functional food with immunity.

Taxonomic Position. FERM P-18099 forms blackish brown colonies on potato-dextrose-agar slant culturing for 7 days at 25 C. The fringe of colonies shows filamentous growth and becomes gradually light blackish brown. The cells are filamentous, and sometimes arthrospores, yeast-like budding conidiospores, oval yeast-like single cells, and, in some time, thick-walled spore cells are formed. The growth temperature is 25° C., and it decomposes hexoses such as glucose, fructose and galactose, sucrose, and starch. The medium becomes conspicuously viscous. Based on FERM P-18099's mycological properties, it is a kind of Aureobasidium pullulans in the black fungus family of deuteromycetes.

Mycological features of the isolated fungus. A colony of FERM P-18099 has a smooth surface at first and grows into a grayish white, mucous and glossy oil drop-like (fat-like), yeast-like material. The filamentous fungus body grows radially from the fringe thereof, leading to crinkled, filamentous and just dendritic growth. This filamentous fungus body grows well not only on the surface of medium, but also in the medium. In a short time, light dark brown specks appear here and there on the surface of colony, which become black specks gradually, and overall surface becomes dark black eventually. On this filamentous fungus body, a lot of light brown, elliptic or oval conidiospores are produced laterally. This conidiospore falls easily in pieces. While the surface of oil drop-like colony puts on the conidiospores here and there.

A medium containing sugars becomes very viscous and produces leather-like black culture moss on the surface of medium with thick colony formation. The optimum growth temperature is 20 to 25° C., and it yields alcohols and organic acids from sugars such as grape sugar and cane sugar. It gives out peculiar fragrance.

Cultural features. Aureobasidium may be cultured on solid or liquid media.

(a) Solid medium: On potato-glucose-agar medium, first, the colony has smooth surface and is transparent, glossy oil drop-like, viscous grayish white yeast-like material. Crinkled, filamentous and just dendritic fungus body grows radially from the fringe of colony, and this filamentous fungus body grows well not only on the surface of medium, but also in the medium. Soon, the dendritic material becomes blackish brown in places. Three to four days after culture, light dark brown specks appear here and there on the surface of colony. These become light dark black gradually thereafter and spread on the overall surface, leading to black eventually as a whole (7 days culture). Besides, on the Czapek agar medium, the growth is slow, but the cultural features are as described above. It takes around 3 weeks for the surface of colony to become black as a whole.

(b) Liquid culture: The fungus body grows here and there in the floating state in potato-glucose medium (3 days culture), the colony increases gradually, and soon (7 days culture), liquid is filled with viscous colonies. And, dark brown fungus moss appears on the wall of pipe, which is formed gradually also on the surface of liquid (15 days culture). This surface pad of fungus is gelatinous, viscous and thick material.

In the Czapek medium, the fungus grows similarly, but the growth is very slow and the number of fungi is few, leading to considerable black fungus moss on the surface of the culture liquid after about 3 weeks.

Culture medium preferably contains between about 3 and 5 mg/ml β-1,3–1,6 glucan.

Morphological features. Young cells are transparent, filamentous, crinkled and dendritic. Black oval spore-like fungus bodies (filamentous) are produced laterally in places. Adherent black spore-like oil drop-like colonies are found. These structures are frangible and fall into pieces when given a shock.

Physiological features. The optimum growth temperature is 20 to 25° C. The culture yields viscous material from carbon sources such as, glucose, sucrose, etc. and alcohols and organic acids from sugars such as glucose. It gives out peculiar fragrance.

Method for Making β-1,3–1,6 glucan (Aureobasidium Medium)

Based on the above information, the β-1,3–1,6 glucan (Aureobasidium medium) to be used in the invention is β-glucan produced by the latest cultural technology, to which we added additional developments and improvements. *Aureobasidium* medium containing β-1,3–1,6 glucan may be produced by culturing *Aureobasidium* in a solid or preferably a liquid culture medium supporting its growth. Such culture media include a carbon source, such as a sugar or carbohydrate, a nitrogen source, such as amino acids or a peptide mixture, and other nutrients, such as salts of sodium, potassium, phosphorous, iron, manganese, magnesium, calcium and sulfur. As mentioned above, culture media include potato-glucose medium and Czapek medium. Other culture conditions, such as those described in U.S. Pat. No. 5,789,579 for culture of a strain producing an α-type acidic polysaccharide, may also be used.

A liquid culture is preferably agitated or aerated. The pH of the culture may range from 2 to 10 and the culture temperature preferably ranges from about 20 to 25° C. *Aureobasidium* medium containing β-1,3–1,6 glucan may be harvested after 1 to 10 days, preferably at the point of maximal production of β-1,3–1,6 glucan. Medium may be separated from cells by centrifugation, for instance, by an initial low speed centrifugation at 5,000 rpm and a high-speed centrifugation at 12,000 rpm. Preferably, the β-1,3–1,6 glucan level in *Aureobasidium* medium is at least 10 times higher than B-glucan levels found in mushrooms. Culture medium may be used directly, after sterilization or filtration, or after further purification.

β-1,3–1,6 glucan in β-1,3–1,6 glucan in *Aureobasidium* medium may be further purified by agglutination with an organic solvent, such as ethanol, or by agglutination with metal ions, such as aluminum ions. Of course, other convention purification methods may used to further purify the β-1,3–1,6 glucan in *Aureobasidium* medium, including precipitation, filtration, chromatography and electrophoresis. Preferably, the β-1,3–1,6 glucan is sterilized by convention methods, for instance, by heat treatment or filtration, prior to use.

While β-glucans may also be extracted from the cell walls of *Aureobasidium*, such cell wall extracts may lose their functional properties upon extraction and fractionation.

The β-1,3–1,6 glucan (*Aureobasidium* medium) of the present invention exhibit unique physical and physiological properties different from other β-glucans produced by other types of fungi, making it particularly useful in commercial and industrial applications, especially in the fields of medical care, health and welfare and in the food industry. The present inventors have found that β-1,3–1,6 glucan (*Aureobasidium* medium) produced with black yeast (*Aureobasidium*) exerts particular regulatory and modulatory effects on the immune system. For instance, β-1,3–1,6 glucan (*Aureobasidium* medium) may be used to increase the numbers of lymphocytes. It may also be used to promote DNA synthesis (cell division), change the morphology of monocytic cells, and modify functional molecules, such as receptors, on the surface of cell membrane. β-1,3–1,6 glucan (*Aureobasidium* medium) also reduces the proliferation of cancer cells and thus exerts an anticancer effect. Moreover, it has also been found that the β-1,3–1,6 glucan (*Aureobasidium* medium) inhibits the proliferation of microbes, such as microbes which adhere to skin surfaces like the hands and feet. Thus, it exerts an antimicrobial and infection-preventative effect.

β-1,3–1,6 glucan (*Aureobasidium* medium) may be used in method for treating inflammatory, infectious or neoplastic diseases. These disease include, for instance, chronic articular rheumatism, collagen disease, newly-risen autoimmune disease, virus or bacterial infection, cancer, invasive or metastatic cancer, oncogenic virus, neuropathy, dementia, Alzheimer's disease, hepatic disease, cirrhosis, viral hepatic disease, cryptogenic intractable disease, life habit disease, diabetes, hypertension, arterial sclerosis, osteoporosis, hemorrhoids, or radiation damage. β-1,3–1,6 glucan (*Aureobasidium* medium) may be administered by topically, orally, by application to a mucous membrane, by inhalation, or by parenteral, subcutaneous or intravenous administration. β-1,3–1,6 glucan (*Aureobasidium* medium) may be formulated into an appropriate form, such as into a sterile or lypholized form, for such modes of administration or into unit dosages. It may also optionally be combined with other pharmaceutical products or drugs.

β-1,3–1,6 glucan (*Aureobasidium* medium) may be used in food products. Advantageously, the beneficial immunological and antimicrobial characteristics of this product may it useful for addition to foods for debilitated or immunocompromised patients, such as aseptic or germless foods for debilitated or immunocompromised patients, such as transplantation patients. For instance, it may be used in foods administered to patients in sterilized rooms after bone marrow transplantation or for burn victims. It may also be used in health foods or nutritional supplements for health maintenance and promotion. It may be used in foods for the aged or debilitated, such as patients who need to maintain their physical strength and disease resistance, or for persons with digestion or assimilation problems, such as deglutition disorders. It may also be used during other types of rehabilitation procedures, or for pregnant women or women under climacteric disturbance (such as menopause). β-1,3–1,6 glucan (*Aureobasidium* medium) may also be incorporated into health foods to maintain a subject's physiological or immunological vitality and balance.

The type of food product into which β-1,3–1,6 glucan (*Aureobasidium* medium) may be applied or incorporated is not particularly limited and may include liquid, semisolid or solid food products. For instance, the β-1,3–1,6 glucan (*Aureobasidium* medium) may be added to hot or cold drinks, including soft drinks, milk products, soy or rice milk products, fruit or vegetable juices; fermented milk products, such as cheeses and yoghurt; ice cream or other frozen products, gelatin or agar products; canned or preserved products, such as jams or jellies, condiments, including catsup, mustards, sauces or gravies, and relishes; canned meats, fruits or vegetables; cereal products, such as rice or wheat products, including noodles, pastas, breads and crackers and cookies. The β-1,3–1,6 glucan (*Aureobasidium* medium) may also be formulated into special nutritional foods, such as hospital foods or nutritional formulas, or as into a nutritional supplement, for instance, into tablet or capsule, optional in combination with other nutrients, such as vitamins or minerals. Such capsules, tablets or pills, advantageously contain between 1 mg and 1,000 mg of β-1,3–1,6 glucan (*Aureobasidium* medium). Solutions of the β-1,3–1,6 glucan (*Aureobasidium* medium) of the present invention may also be applied or sprayed on the surfaces of foods, such as fresh fruits and vegetables to prevent or inhibit microbial contamination or spoilage.

The β-1,3–1,6 glucan (*Aureobasidium* medium) may also be incorporated into personal care products, such as toothpastes or mouthwash, or into a cosmetic, such as shampoo, soap, powder, such as a body or face powder, a gel, a film, a masque, a cosmetic cream, or a lotion. Such compositions and products may also be used to treat topical skin disorders, infections, or bums, including sunburns or UV irradiation, or to protect the connective skin tissue.

Products, including pharmaceutical, food, personal care and cosmetic products, contain about 0.001 mg gr to 100 mg/gr of β-1,3–1,6 glucan from *Aureobasidium* (culture medium) and a preferable amount of *Aureobasidium* culture medium to be used in such products and compositions is from 0.1 to 100 parts by weight %. *Aureobasidium* culture medium preferably contains from about 3 to 5 mg/ml β-1,3–1,6 glucan. Accordingly, such products may also preferably contain from about 0.003 to 5 mg/ml β-1,3–1,6 glucan. Foods preferably contain about 5 to 100 parts by weight/100 parts total weight of *Aureobasidium* culture medium.

β-1,3–1,6 glucan (*Aureobasidium* medium) may be formulated into a pharmaceutical product, such as a product for modulating the immune system, or for treating a microbial or inflammatory disease. The β-1,3–1,6 glucan (*Aureobasidium* medium) may be ingested, applied topically or parenterally, or administered directly to the site or biological compartment containing cancer cells. It may also be incorporated into a diagnostic product, as a auxiliary reagent (e.g. a buffer, stabilizer or preservative), or as a active component for the diagnosis of diseases associated with altered levels of glucans.

Moreover, as shown below, β-1,3–1,6 glucan (*Aureobasidium* medium) may be used in products and compositions for the prevention of nosocomial infection or removal of environmental pollutants, for instance, into agents that prevent the propagation of microbes. It may also be used as a sanitizer or disinfectant, for instance, for cleaning the bodies of persons who are aged or infirm and cannot bathe. The *Aureobasidium* culture medium may also be used undiluted as a disinfectant. Additionally, it may be used to treat hospital personnel, patients, surfaces, equipment, supplies or instruments in order to prevent nosocomial infections. Moreover, it may be used to remove environmental pollutants, such as internal secretion detractors, environmental hormones, toxins, heavy metals, and dioxins. As a sanitizer or disinfectant, β-1,3–1,6 glucan (*Aureobasidium* medium) may be added to water or other conventional cleaning or disinfectant solutions, including detergent or soap solutions.

EXAMPLES

The following examples illustrate the effects of β-1,3–1,6 glucan (*Aureobasidium* medium) on the immune system.

To test these effects, peripheral lymphocytes were conventionally separated from peripheral blood of normal and healthy subjects. Separated lymphocytes were divided into control groups, which were not treated with β-1,3–1,6 glucan (*Aureobasidium* medium) and into experimental groups treated with β-1,3–1,6 glucan (*Aureobasidium* medium).

Control and experimental groups were cultured in an appropriate culture medium (RPMI1640 containing 10% fetal calf serum (FCS) and 20% human serum (HS)) for a fixed period to investigate the influence of β-1,3–1,6 glucan (*Aureobasidium* medium) on the numbers of lymphocytes, cell division of lymphocytes, production level of IgG antibody and on the production of cytokines. Moreover, morphological change of the peripheral blood lymphocytes was observed using a phase microscope. Moreover, the effects of β-1,3–1,6 glucan (*Aureobasidium* medium) treatment on lymphocytic cell surface molecules (receptors) was determined.

Additionally, the effects of β-1,3–1,6 glucan (*Aureobasidium* medium) on different types of cancer cells, such as different leukemia cell lines, were determined by comparison of control cancer cells receiving no treatment with β-1,3–1,6 glucan (*Aureobasidium* medium), with experimental samples of the same types of cancer cells treated with β-1,3–1,6 glucan (*Aureobasidium* medium). The number of lymphocytes was observed and calculated under phase microscope by using hemocytometer. See FIG. 1.

The capacity of control or treated lymphocytes to synthesize DNA was determined by a conventional method. Namely, it was measured by the uptake or incorporation of tritiated thymidine (3H-thymidine) as measured by scintillation counting. Uptake is represented by the number of counts per minute, cpm. See Tables 4 and 5.

The production level of antibody from the lymphocytes in human peripheral blood with β-1,3–1,6 glucan (*Aureobasidium* medium), that is, the production level of IgG antibody from B cells being immunocytes was determined by using enzyme antibody technique. Namely, according to the usual method, the amount of antibody in actual medium was determined by using double antibody enzyme antibody, enzyme immunoassay (EIA) technique. There are many methods for determining the amount of antibody, for example, method using plaque technique, Ouchterlony technique, fluorescent antibody technique, etc. However, the EIA technique used in the examples has very high sensitivity and allows to determine even with small amount of material, hence it is a method used routinely as an immunological examination technique. See Table I which shows effects of β-1,3–1,6 glucan (*Aureobasidium* medium) on IgG production.

For investigating the influence of β-1,3–1,6 glucan (*Aureobasidium* medium) on lymphocytes, the production levels of particular cytokines, such as interleukin and interferon, was determined by an enzyme-antibody technique. The enzyme-antibody technique measures the amounts of serum and cytokines in medium. Commercial kits for this technique are available from various firms. The levels of cytokines, such as interleukin 1, 2, 4, 6, and interferon were determined using this method. Evaluation of the effects of β-1,3–1,6 glucan (*Aureobasidium* medium) on particular aspects of the immune system was done by a determination of the amounts of and dynamics of cytokine production or release. These results are presented in Tables II and III.

For investigating the morphological changes of lymphocytes treated with β-1,3–1,6 glucan (*Aureobasidium* medium), the lymphocytes cultured with β-1,3–1,6 glucan (*Aureobasidium* medium) are observed under phase microscope. Following this, their morphological change, in particular, shape of cells and change in the ruffle structure of cell surface are observed and taken into photographs. See FIG. 2.

With respect to the investigation on the change in dynamics of lymphocyte or surface molecule (receptor) of model cell cultured with β-1,3–1,6 glucan (*Aureobasidium* medium), the flow cytophotometry technique (fluorescence activated cell sorter: FACS) is used. This advantageous method is capable of analyzing the dynamics of cell surface antigen and receptor as an immunologically analyzing means. This determination is conducted by using monoclonal antibody that reacts specifically with cell surface and antibody labeled with fluorescence, and, actually, the fluorescence intensity is image analyzed with computer after the reflection of laser beam was taken-in, and the results are converted to histogram. See FIG. 7.

The influence of β-1,3–1,6 glucan (*Aureobasidium* medium) on the proliferation of cancer cells, in particular, leukemia cells is judged by the life and death of cancer cells cultured with β-1,3–1,6 glucan (*Aureobasidium* medium) for a fixed period. Namely, according to this method, the leukemia cells cultured with β-1,3–1,6 glucan (*Aureobasidium* medium) are collected and the life and death of cancer cells are counted by using hemocytometer to investigate the extent of proliferation of cancer cells. In some experiments, cells are stained actually by using stain solution to investigate the influence of β-1,3–1,6 glucan (*Aureobasidium* medium) on the extent of proliferation of cancer cells. See FIGS. 3–6.

For investigating the effect of β-1,3–1,6 glucan (*Aureobasidium* medium) on the removal of environmental microbes, a palm stamp on a conventional agar medium was used. This method counts the number of microbial colonies on the palm stamp on the agar medium as a measure of number of environmental microbes adhered to the skin surface. Conventional tryptosoy agar medium (medium: trypton, soy peptone, sodium chloride, agar) was used as an agar medium. However, different media may be selected, for instance, for investigating *staphylococcus* (a main microbe in nosocomial infections), mannite-salt-agar medium is used. For *Salmonella*, coliform bacteria, etc. involved in food poisoning, a selective agar media such as SS (*Salmonella-Shigella*) agar medium and Drigalski agar medium, and the like, may be used. In respective agar media, pH indicators such as phenol red and BTB (bromthymol blue) are contained, making it possible to know the proliferation of microbes by judging the color of medium. See FIG. 8.

Example 1

Influence of β-1,3–1,6 glucan (*Aureobasidium* Medium) on Numbers of Lymphocytes in Peripheral Blood Various concentrations of β-1,3–1,6 glucan (*Aureobasidium* medium) were added to the lymphocytes in healthy and normal human peripheral blood, which were cultured for 6 to 7 days at 37° C. After culture, the number of lymphocytes was counted by using hemocytometer. As a result, as shown in FIG. 1, β-1,3–1,6 glucan (*Aureobasidium* medium) at a fixed concentration tended to increase the number of lymphocytes in peripheral blood about 1.2 to 1.5 times compared with control group (group without β-1, 3–1,6 glucan).

Moreover, lymphocytes in human peripheral blood were taken out from healthy and normal person who continued to drink β-1,3–1,6 glucan (*Aureobasidium* medium) for longer than 3 years and an optimum concentration of β-1,3–1,6 glucan (*Aureobasidium* medium) was added again in vitro to investigate the morphological change thereof. Conspicuous blast formation (image of cell division) was recognized for the group with β-1,3–1,6 glucan (*Aureobasidium* medium) added, compared with the group without addition (FIG. 2: Photographs).

Example 2

Influence of β-1,3–1,6 glucan (*Aureobasidium* Medium) on Production of IgG Antibody Various concentrations of β-1,3–1,6 glucan (*Aureobasidium* medium) were added to the lymphocytes in healthy and normal human peripheral blood, which were cultured for 7 days at 37° C. After culture, the concentration of antibody (IgG) in the supernatant of medium was examined by enzyme antibody technique using the double antibody EIA technique. No significant effect on the production of human IgG antibody by lymphocytes in human peripheral blood was seen. This result suggests that β-1,3–1,6 glucan (*Aureobasidium* medium) is unlikely to cause adverse effects, such as decreases in antibody production in vivo.

TABLE 1

Influence of β-1.3–1.6 glucan (*Aureobasidium* medium) administration IgG antibody levels.

| Concentration of β-1.3–1.6 glucan (mg/ml) | Concentration of IgG antibody produced (ng/ml) |
|---|---|
| 0 | 668 |
| 7.5 | 835 |
| 0.75 | 592 |
| 0.35 | 663 |
| 0.18 | 553 |

Example 3

Influence of β-1,3–1,6 glucan (*Aureobasidium* Medium) on the Production of Cytokines IL-1β or IL-2.

A fixed concentration (final concentration 400 times) of β-1,3–1,6 glucan (*Aureobasidium* medium) was added to the lymphocytes in healthy and normal human peripheral blood, which was cultured for 5 days at 37° C. After culture, the concentration of cytokines (interleukin 1: IL-1 and interleukin-2: IL-2) in the supernatant of medium was examined by enzyme antibody technique (enzyme immunoassay: EIA technique). As a result, as shown in Table 2, no remarkable difference was recognized in the level of production between the group with β-1,3–1,6 glucan (*Aureobasidium* medium) added and the group without addition. This result also suggests that the β-1,3–1,6 glucan (*Aureobasidium*) would be unlikely to cause adverse effects in vivo, such as effects associated with the production of IL-1β or IL-2.

TABLE 2

Influence of β-1.3–1.6 glucan (*Aureobasidium* medium) on the production of cytokines

| Culture | Production of cytokine | |
|---|---|---|
| | IL-1β | IL-2 |
| No addition | <10 pg/ml | <0.8 U/ml |
| Addition with β-1.3–1.6 glucan (*Aureobasidium* medium) | <10 pg/ml | <0.8 U/ml |

Example 4

Influence of β-1,3–1,6 glucan (*Aureobasidium* Medium) on the Production of Cytokine (2)

A fixed concentration (final concentration 20 times) of β-1,3–1,6 glucan (*Aureobasidium* medium) was added to the monocytic model cell strain, which was cultured for 2 to 4 days at 37° C. After culture, the concentration of various cytokines (interleukin 1β: IL-1β, interleukin-4: IL-4, interleukin-2: IL-2, interleukin-6: IL-6 and interferon γ: IFN-γ) in the supernatant of medium was examined by enzyme antibody technique (enzyme immunoassay: EIA technique). As a result, as shown in Table 3, about 20 times or higher level of production of IL-6 was recognized for the group with β-1,3–1,6 glucan (*Aureobasidium* medium) added, compared with the group without addition. However, these results suggest that administration of β-1,3–1,6 glucan would not be expected to induce side-effects associated with interleukin 1 β (IL-1 β), interleukin-4 (IL-4), interleukin-2 (IL-2), or interferon γ (IFN-γ).

TABLE 3

Influence of β-1.3–1.6glucan (Aureobasidium medium) on the production of various cytokines

| Culture | Production of cytokine | | | | |
| --- | --- | --- | --- | --- | --- |
| | IL-1β | IL-2 | IL-4 | IL-6 | IFN-γ |
| No addition | <10 pg/ml | <0.8 U/ml | <2.0 pg/ml | 2.0 pg/ml | <0.1 IU/ml |
| Addition with β-1.3–1.6 glucan (Aureobasidium medium) | <10 pg/ml | <0.8 U/ml | <2.0 pg/ml | 49.5 pg/ml | <0.1 IU/ml |

Example 5

Influence of β-1,3–1,6 glucan (Aureobasidium Medium) on Normal Lymphocyte Cell Division as Measured by DNA Synthesis β-1,3–1,6 glucan (Aureobasidium medium) (final concentration 400 times) was added to lymphocytes from normal and healthy human peripheral blood and also to the lymphocytes of a patient after bone marrow transplantation. The lymphocyte samples were cultured for 5 days at 37° C. After 5 days, tritiated thymidine (1 μCi) was added to these samples.

As shown in Table 4, normal lymphocytes treated with β-1,3–1,6 glucan (Aureobasidium medium) exhibited increased cell division as measured by an average stimulation of DNA synthesis of about 4.5-times, compared to untreated normal lymphocytes.

TABLE 4

Influence of β-1.3–1.6 glucan (Aureobasidium medium) on cell division as measured by DNA synthesis in lymphocytes from healthy and normal subjects.

| Lymphocyte | Capability of DNA synthesis (cpm) | | SI |
| --- | --- | --- | --- |
| in peripheral blood | No addition | Addition with β-1.3–1.6 glucan (Aureobasidium medium) | (Stimulation index) |
| SA | 624 | 851 | 1.4 |
| TS | 444 | 2067 | 4.7 |
| YA | 460 | 1232 | 2.7 |
| IS | 238 | 2177 | 9.1 | cpm: Count per minute
SI: Stimulation Index

TABLE 5

Influence of β-1.3–1.6 glucan (Aureobasidium medium) on cell division as measured by DNA synthesis in patients after bone marrow transplantation.

| | | Capability of DNA synthesis stimulation index (SI) Stimulation with β-1.3–1.6 glucan (Aureobasidium medium) | |
| --- | --- | --- | --- |
| Lymphocyte | Transplantation form | Primary Stimulation | Secondary Stimulation |
| SU | Patient with bone marrow transplantation (Allogenic bone marrow transplantation) | 2.7 | 2.7 |
| AI | Patient with bone marrow transplantation (Allogenic bone marrow transplantation) | 3.6 | 5.2 |
| KM | Patient with bone marrow transplantation (Allogenic bone marrow transplantation) | 3.6 | 2.1 |
| NO | Patient with bone marrow transplantation (Autologous bone marrow transplantation) | 2.3 | 2.7 |
| TM | Patient with bone marrow transplantation (Allogenic bone marrow transplantation) | 1.2 | 0.6 |
| ZT | Patient with bone marrow transplantation (Autologous bone marrow transplantation) | 2.0 | 2.2 |
| YK | Patient with cord marrow transplantation (Allogenic transplantation) | 1.0 | 1.3 |
| SF | Patient with cord marrow transplantation (Allogenic transplantation) | 1.2 | 0.9 |

SI: Stimulation index

Table 5 shows that lymphocytes from a majority of bone marrow transplantation patients also showed stimulation of cell division as measured by DNA synthesis. The stimulation index in Tables 4 and 5 represents the ratio of counts (cpm) in lymphocyte samples that were treated with β-1,3–1,6 glucan (Aureobasidium medium) over untreated controls.

Example 6

Influence of β-1,3–1,6 glucan (Aureobasidium Medium) on the Proliferation of Cancer Cells β-1,3–1,6 glucan (Aureobasidium medium) (final concentration 20 times) was added to various leukemia cells, which were cultured for 1 to 3 days at 37° C. After culture, the number of leukemia cells was counted by using hemocytometer to investigate the influence on the proliferation of leukemia cell. As shown in FIGS. 3–6, addition of β-1,3–1,6 glucan (*Aureobasidium* medium) directly inhibited the proliferation of cancer (leukemia) cells. These data suggest the direct killing of cancer (leukemia) cells, for instance, by induction of programmed death (apoptosis), as other components of the immune system were absent.

Example 7

Influence of β-1,3–1,6 glucan (*Aureobasidium* Medium) on the Dynamics of Cell Surface Molecule (Receptor Molecule) in Monocyte/Macrophage Model System β-1,3–1,6 glucan (*Aureobasidium* medium) (final concentration 20 times) was added to the cells in a monocyte/macrophage model system. Cells were cultured for 24 hours at 37° C. After 24 hours, the cells were collected and the dynamics of various human cell membrane antigens (receptor: CD antigen) were analyzed by indirect fluorescence antibody technique (flow cytophotometry technique) that uses various monoclonal antibodies. As shown in FIG. 7 the levels of CD11a and CD49d molecules on the surface of cells in monocyte/macrophage model system cultured with β-1,3–1,6 glucan (*Aureobasidium* medium) were down-regulated.

Example 8

Effect of β-1,3–1,6 glucan (*Aureobasidium* Medium) on the Prevention of Propagation (Proliferation) of Environmental Microbes The removal or inactivation of environmental microbes adhered to surfaces or organisms is an important subject in the fields of medical care, health and welfare. Such removal or inactivation is particularly important for the prevention of nosocomial infections. Therefore, the antimicrobial effects of β-1,3–1,6 glucan (*Aureobasidium* medium) on the proliferation of environmental microbes adhered to hands, feet and body, was evaluated using a palm stamp technique involving contacting the palm of the hand with a solid microbial medium. The hands of control subjects were contacted to the medium for about 20 seconds. The hands of those in the experimental group were first wiped with a solution containing β-1,3–1,6 glucan (*Aureobasidium* medium) and dried for about 5 minutes prior to contact with the medium. Similarly to the control group, the hands were then contacted with the nutritional solid medium for about 20 seconds.

The solid medium was cultured for 1 to 2 days at room temperature, and the proliferation of microbes (number of colonies) was observed. As shown in FIG. 8 the palm stamps of hands treated with β-1,3–1,6 glucan (*Aureobasidium* medium) showed far fewer microbial contaminants. This shows that the β-1,3–1,6 glucan (*Aureobasidium* medium) inhibits the proliferation of environmental microbes and can be used as a sanitizer or the bodies of persons who are aged or infirm and cannot bathe and also for the prevention of nosocomial infections and removal of environmental pollutants.

Modifications and other Embodiments

Various modifications and variations of the described glucan products, compositions and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the chemical, biological, medical, environmental, cosmetic or food arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specifically, priority documents Japanese Patent Application 2000-42310, filed Nov. 9, 2000, is hereby incorporated by reference.

What is claimed is:

1. A method for producing β1,3–1,6 glucan comprising: culturing an *Aureobasidium* fungus strain FERM P18099 that produces β1,3–1,6 glucan in a culture medium for a time and under conditions suitable for production of β1,3–1,6 glucan in said culture medium.

2. The method of claim 1, further comprising recovering β1,3–1,6 glucan from the culture medium.

3. A culture medium produced by the method of claim 1.

4. The culture medium of claim 3, wherein said medium contains about 3–5 mg/ml of *Aureobasidium* β1,3–1,6 glucan.

5. A composition comprising from about 0.1 to 100 parts by weight of the undiluted culture medium of claim 3.

6. The A food product comprising an isolated or purified β1,3–1,6 glucan obtained from *Aureobasidium* strain FERM P18099 medium, which is a milk product.

7. The food product of claim 6, which is a soy or rice milk product.

8. The food product of claim 6, which is a fermented milk product.

9. The food product of claim 6, which is yogurt.

10. The food product of claim 6, which is cheese.

11. The food product of claim 6, which is ice cream or a frozen milk product.

* * * * *